(12) United States Patent
Burkhart

(10) Patent No.: US 7,959,649 B2
(45) Date of Patent: *Jun. 14, 2011

(54) SUTURE ANCHOR DEVICE, KIT AND METHOD

(75) Inventor: Stephen S. Burkhart, San Antonio, TX (US)

(73) Assignee: Arthrex, Inc., Naples, FL (US)

( * ) Notice: Subject to any disclaimer, the term of this patent is extended or adjusted under 35 U.S.C. 154(b) by 658 days.

This patent is subject to a terminal disclaimer.

(21) Appl. No.: 11/637,383

(22) Filed: Dec. 12, 2006

(65) Prior Publication Data

US 2007/0142861 A1     Jun. 21, 2007

Related U.S. Application Data

(63) Continuation of application No. 10/412,205, filed on Mar. 31, 2003, now abandoned.

(51) Int. Cl.
*A61B 17/04*     (2006.01)
(52) U.S. Cl. ........................... 606/232; 606/144
(58) Field of Classification Search .................. 606/232, 606/148, 139, 144, 145, 146
See application file for complete search history.

(56) References Cited

U.S. PATENT DOCUMENTS

| | | |
|---|---|---|
| 4,741,330 A | 5/1988 | Hayhurst |
| 4,961,741 A | 10/1990 | Hayhurst |
| 5,037,422 A | 8/1991 | Hayhurst |
| 5,041,129 A | 8/1991 | Hayhurst |
| 5,078,731 A | 1/1992 | Hayhurst |
| 5,100,415 A | 3/1992 | Hayhurst |
| 5,108,399 A | 4/1992 | Eitenmuller |
| 5,116,337 A | 5/1992 | Johnson |
| 5,129,904 A | 7/1992 | Illi |
| 5,152,790 A | 10/1992 | Rosenberg |
| 5,224,946 A | 7/1993 | Hayhurst |
| 5,236,431 A | 8/1993 | Gogolewski |
| 5,236,445 A | 8/1993 | Hayhurst |
| 5,258,016 A | 11/1993 | DiPoto |
| 5,269,809 A | 12/1993 | Hayhurst |
| 5,417,691 A | 5/1995 | Hayhurst |
| 5,443,482 A | 8/1995 | Stone |
| 5,474,572 A | 12/1995 | Hayhurst |
| 5,496,348 A * | 3/1996 | Bonutti .................. 606/232 |
| 5,545,180 A | 8/1996 | Le |
| 5,569,306 A | 10/1996 | Thal |
| 5,573,548 A | 11/1996 | Nazre |
| 5,601,557 A | 2/1997 | Hayhurst |
| 5,618,314 A | 4/1997 | Harwin |
| 5,626,613 A | 5/1997 | Schmieding |
| 5,643,320 A | 7/1997 | Lower et al. |
| 5,647,874 A | 7/1997 | Hayhurst |
| 5,658,313 A | 8/1997 | Thal |

(Continued)

*Primary Examiner* — (Jackie) Tan-Uyen T Ho
*Assistant Examiner* — Alexander Orkin
(74) *Attorney, Agent, or Firm* — Jackson Walker, LLP

(57) ABSTRACT

A suture anchor and kit for anchoring a suture member to human bone in an interference fit. A suture anchor includes a threaded portion and has a head at the proximal end thereof, the head being generally circular. A tip is located at a distal end of the shank. The shank is at least partially threaded and includes walls defining a reel portion. The shank also includes walls for engaging a suture, the walls for engaging the suture typically adjacent walls defining the reel portion. The head typically includes walls for engaging a drive tool. The kit includes a drive tool for rotating the suture anchor when a suture member is engaged with the walls for engaging the suture such that rotation of the anchor causes the suture material to wrap around the reel portion of the shank.

19 Claims, 6 Drawing Sheets

U.S. PATENT DOCUMENTS

| | | | |
|---|---|---|---|
| 5,665,112 A | 9/1997 | Thal | |
| 5,683,419 A | 11/1997 | Thal | |
| 5,702,397 A * | 12/1997 | Goble et al. | 606/232 |
| 5,702,398 A * | 12/1997 | Tarabishy | 606/232 |
| 5,707,394 A | 1/1998 | Miller | |
| 5,709,708 A | 1/1998 | Thal | |
| 5,720,765 A | 2/1998 | Thal | |
| 5,720,766 A | 2/1998 | Zang | |
| 5,728,136 A | 3/1998 | Thal | |
| 5,733,307 A | 3/1998 | Dinsdale | |
| 5,810,848 A | 9/1998 | Hayhurst | |
| 5,814,070 A | 9/1998 | Borzone | |
| 5,814,073 A | 9/1998 | Bonutti | |
| 5,824,011 A | 10/1998 | Stone | |
| 5,868,789 A | 2/1999 | Huebner | |
| 5,899,920 A | 5/1999 | DeSatnick | |
| 5,904,704 A | 5/1999 | Goble | |
| 5,906,624 A | 5/1999 | Wenstrom | |
| 6,013,077 A * | 1/2000 | Harwin | 606/232 |
| 6,139,565 A * | 10/2000 | Stone et al. | 606/232 |
| 6,267,766 B1 * | 7/2001 | Burkhart | 606/232 |
| 6,540,750 B2 * | 4/2003 | Burkhart | 606/232 |
| 6,656,182 B1 | 12/2003 | Hayhurst | |
| 2003/0109900 A1 * | 6/2003 | Martinek | 606/219 |
| 2003/0229350 A1 * | 12/2003 | Kay | 606/72 |
| 2004/0093031 A1 * | 5/2004 | Burkhart et al. | 606/232 |
| 2005/0090827 A1 * | 4/2005 | Gedebou | 606/72 |

* cited by examiner

SUTURE ANCHOR DEVICE, KIT AND METHOD

This patent application is a continuation of and claims priority from U.S. patent application Ser. No. 10/412,205, filed Mar. 31, 2003 now abandoned; which is incorporated hereby by reference; and claims priority from U.S. Pat. No. 6,540,750, issued Apr. 1, 2003; and U.S. Pat. No. 6,267,766, issued Jul. 31, 2001.

BACKGROUND OF THE INVENTION

1. Field of the Invention

Applicant's invention relates to a device, method and kit for repairing tissue, namely for selectively positioning a suture-bearing tissue adjacent a bone mass.

2. Background Information

When soft tissue, such as tendons and ligaments, are torn away from the bone, surgery may be required to repair the tear. Typically, a suture member is threaded through the torn tissue and through a tunnel drilled in the bone mass. The suture material is drawn up and tied so that the torn tissue lays adjacent the bone mass in proper position to heal.

A number of assemblies have been provided to anchor tissue to a bone mass. These devices are usually attached to the bone mass through the use of open incisions or, sometimes, arthroscopic surgical techniques. Arthroscopic surgery is advantageous compared to the use of open surgery because of the decreased pain and quicker recovery period. However, the invention may be used advantageously with open surgery as well.

The various assemblies used for attaching soft tissue to the bone include screws, staples, suture anchors, cement, and sutures alone. The suture anchor is a small device, typically insertable arthroscopically through a cannula to the repair site to anchor the suture to a bone.

That is, a suture is passed through the soft tissues and inserted into a suture anchor in the base. Such a suture anchor assembly is disclosed in U.S. Pat. No. 5,683,419. This suture anchor assembly includes two main components: an anchor sleeve, which can have a closed pointed drill end or be totally cylindrical in shape, ribbed, or threaded on its exterior for attachment to the bone; and a spike or plug with one end that allows for easy puncturing of soft tissue and a second end for attachment of the suture material. The pointed first end of the spike or plug allows it to be insertable to the sleeve, which sleeve has been inserted into the bone.

A second device is disclosed in U.S. Pat. No. 5,904,704 and includes a suture anchor assembly, including a suture anchor and a tool for deploying the suture anchor in the bone. The suture extends from and is anchored to the bone. The suture anchor has a drill portion and a thread portion, and a suture attachment portion distal to the pointed portion.

None of the prior art provides for a suture anchor that includes a reel portion adjacent suture-receiving walls in a manner that allows the threading of the anchor member into the bone while the suture material simultaneously winds around the reel portion of the suture anchor to draw up the suture and the corresponding soft tissue to which the suture is engaged so as to selectively position the soft tissue adjacent the bone.

None of the prior art shows a reel portion capable of providing an interference fit of suture between the bone and anchor.

Applicant provides a unique suture anchor, including a reel portion thereon, a unique method of using the suture anchor to selectively position, by rotation of the suture anchor and gathering the suture material on the reel portion thereof, the suture bearing tissue, and a novel kit providing a suture anchor and a tool for rotating the suture anchor. Applicant's device may be used without the necessity of tying suture knots arthroscopically or, indeed, may be used without tying suture knots at all.

Applicant's novel suture anchor, method, and kit overcome problems encountered in prior art suture anchors and provide a relatively easy method of arthroscopically reattaching torn or displaced tissue to a bone mass.

Figure 3:
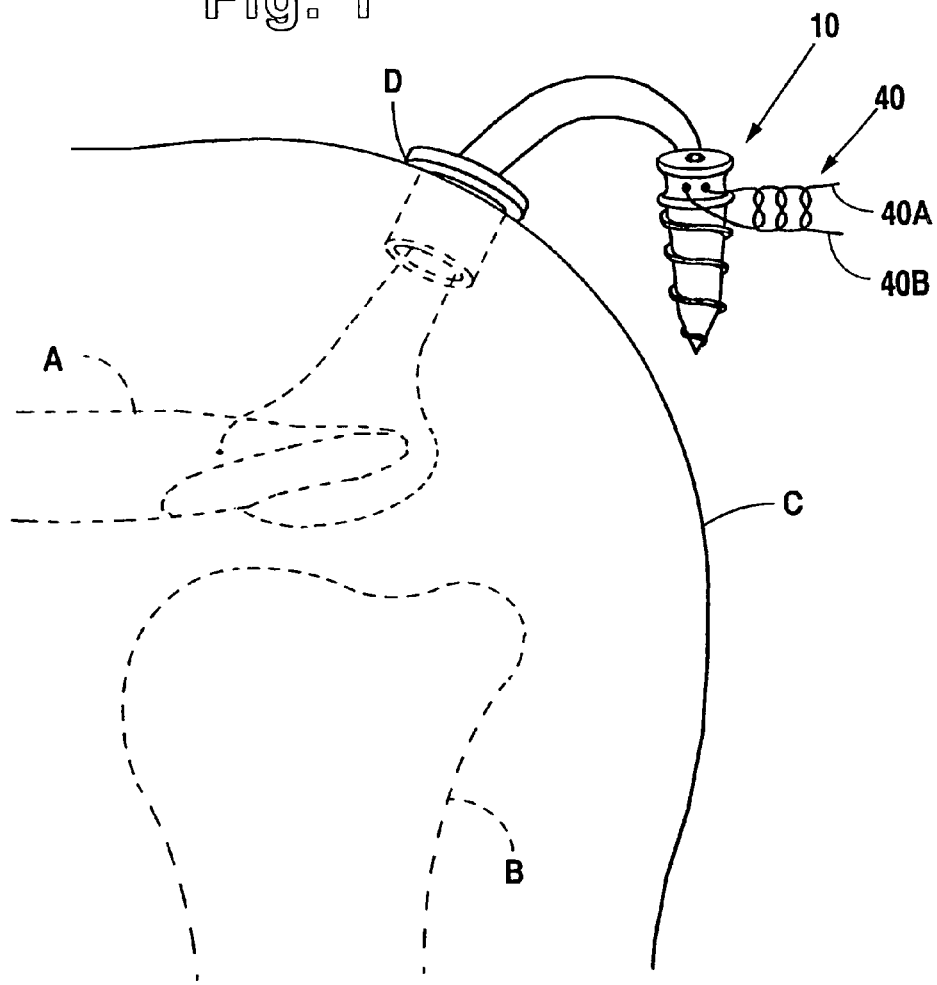
FIG. 3 is a side perspective view of a shoulder C (partially cut-away) having torn tissue A therein, having a bone mass B, the shoulder open through an incision through which is inserted a cannula D, the perspective view illustrating the engagement of suture material 40 to suture anchor 10.
Figure 4:
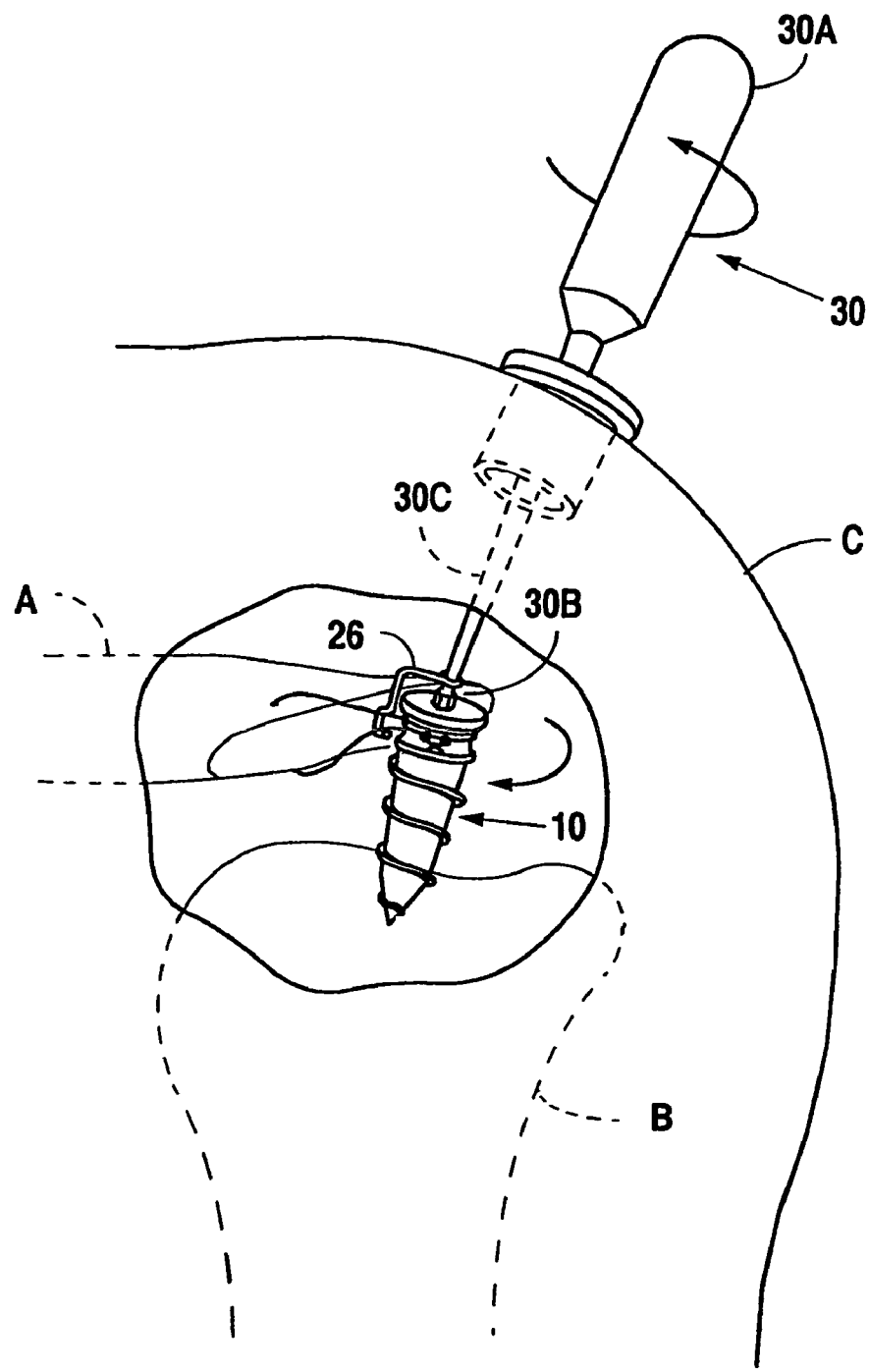

FIG. 4 is a view of the shoulder C of FIG. 3 which illustrates the use of Applicant's tool 30 for engaging the anchor 10 as the anchor is inserted into bone B, the perspective view also illustrating the use of an out-rigger 26 on the tool to help guide the suture.

Figure 5:
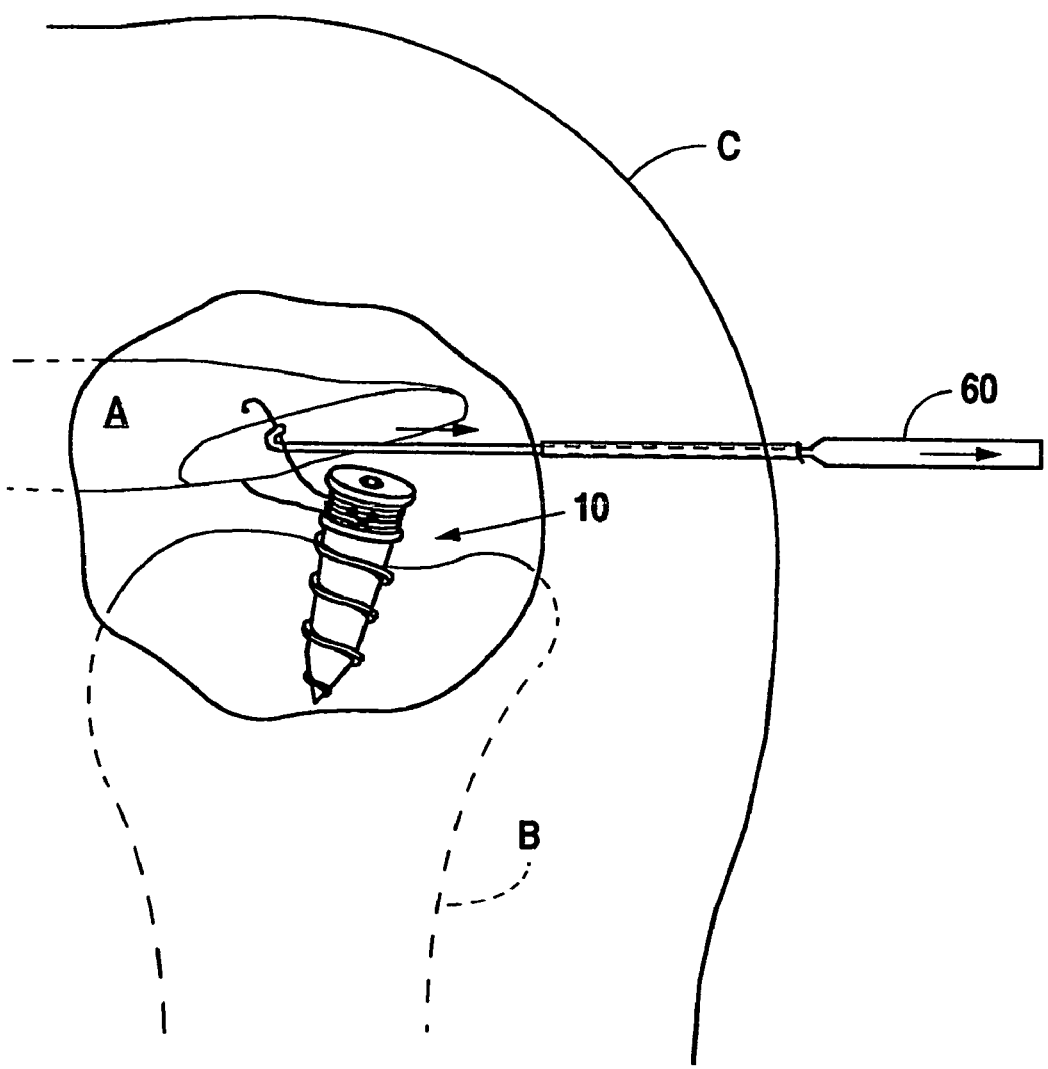

FIG. 5 is an illustration of an additional hook tool 60 for use with Applicant's present invention.

Figure 6:
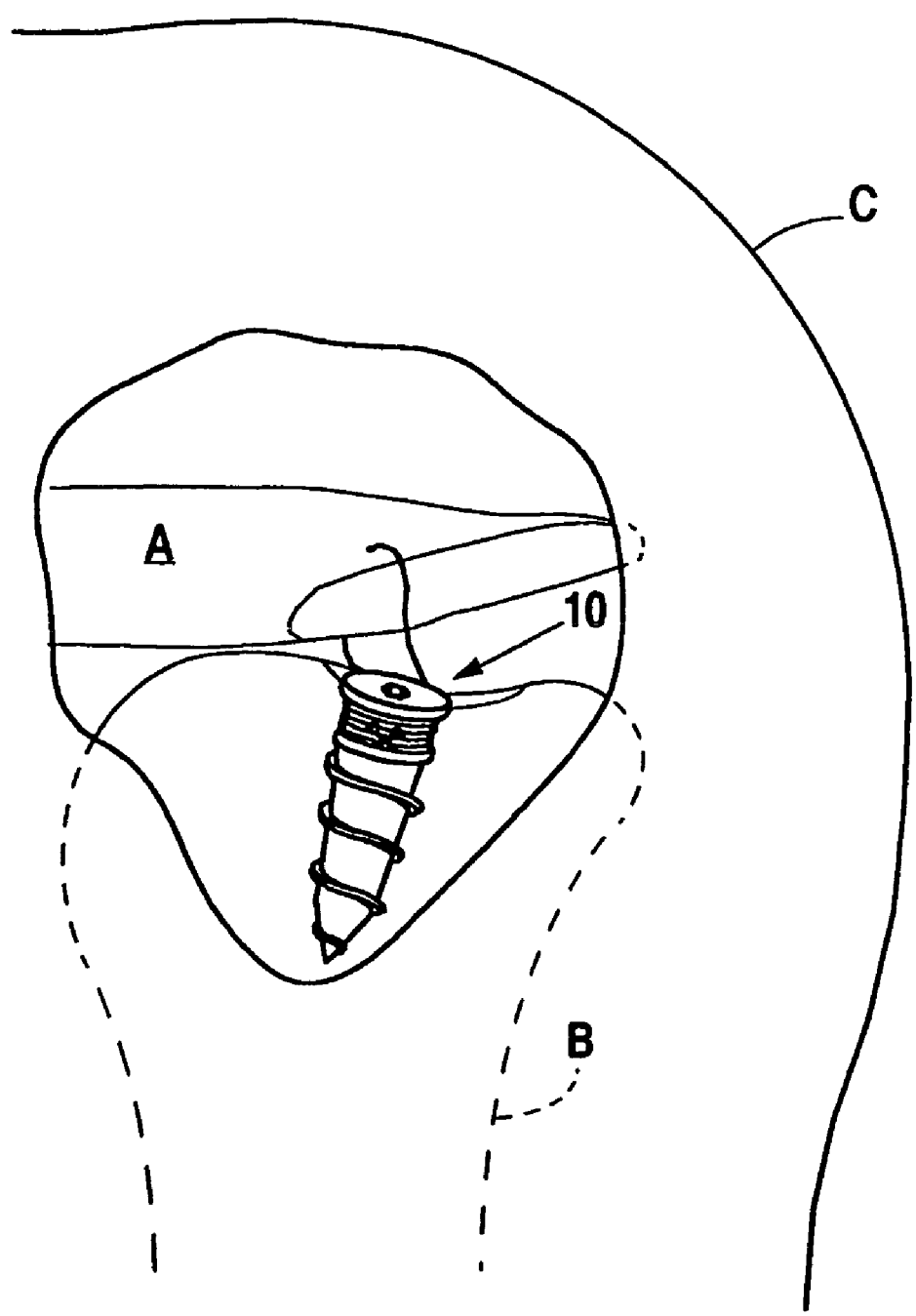

FIG. 6 illustrates the shoulder mass and tissue after the tissue has been selectively located adjacent the bone by reeling surgery material onto the suture anchor in the manner set forth in Applicant's present invention.

Figure 7:
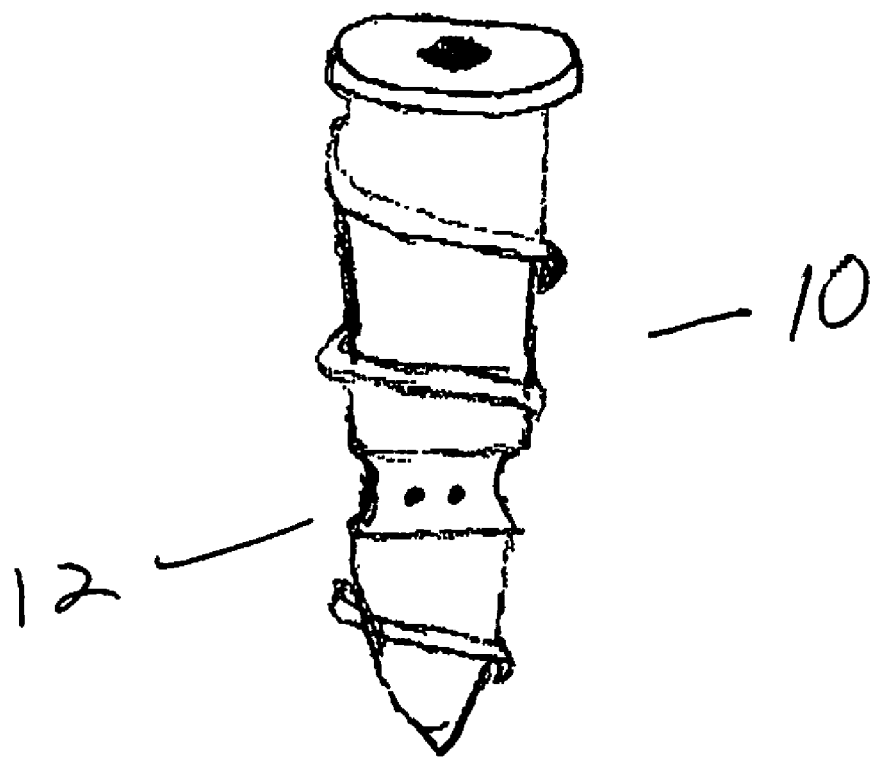

FIG. 7 shows an embodiment with a reel portion located along the shank near the tip although the reel could be located anywhere along the shank.

DETAILED DESCRIPTION OF THE PREFERRED EMBODIMENT

Figure 1:
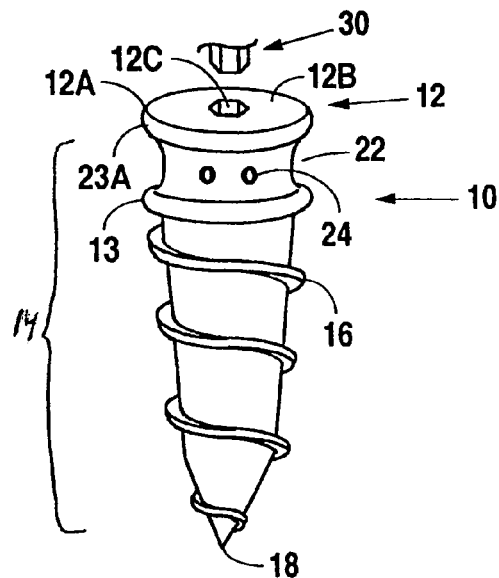
FIG. 1 is a side elevational view of the suture anchor of Applicant's present invention holes in any non-head portion.
Figure 2:
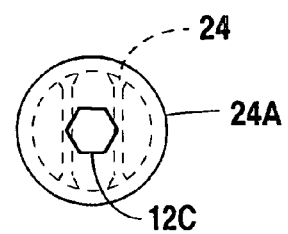
FIG. 2 is a top elevational view of the suture anchor of FIG. 1.

In viewing FIGS. 1 through 3 it is seen that Applicant's present invention includes a unitary, longitudinal suture anchor 10, typically made of titanium, stainless steel, plastic, allograft bone, or other suitable material, including a bio-absorbable material. The suture anchor is seen to have a generally circular head 12, the head typically having an outer edge 12A, an upper surface 12B, and walls 12C for engaging any type of mating tool as set forth in more detail below.

Applicant's novel suture anchor 10 includes a shank portion 14 located distal to the head 12, the shank portion 14 having threads 16 on at least a portion thereof, the shank portion 14 terminating at a tip 18. The shank portion 14 also includes a reel portion 22, typically having adjacent walls 23 defining a suture receiving portion. The particular configuration of the walls 23 here include a pair of holes 24 going from one portion of the outer surface of the shank portion 14 to a second portion of the outer surface of the shank portion 14 (see FIG. 2) transverse to the longitudinal axis of the shank portion 14 and being dimensioned to receive a suture member 40 therethrough. That is, the holes are in a non-head portion of the anchor.

The reel portion 22 typically has raised upper walls 23 proximal (towards the head 12) adjacent thereto to keep the gathered suture member 40 from slipping off the top of the wall 23. It may also have lower walls 13 which, in conjunction with upper walls, help keep the suture winding on the anchor. It is noted that the lower walls in the embodiment illustrated in FIGS. 1-3 have about the same radius as the upper walls, while the lower walls in the embodiment illustrated in the remaining figures have a diameter less than the upper walls.

Figure 3A:
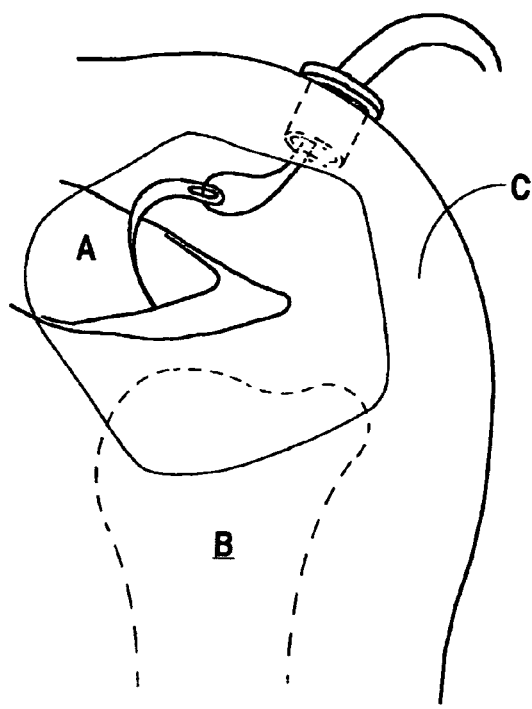
FIGS. 3A and 3B illustrate perspective views of the shoulder (partially cut-away) illustrating two steps of Applicant's present invention.
Figure 3B:
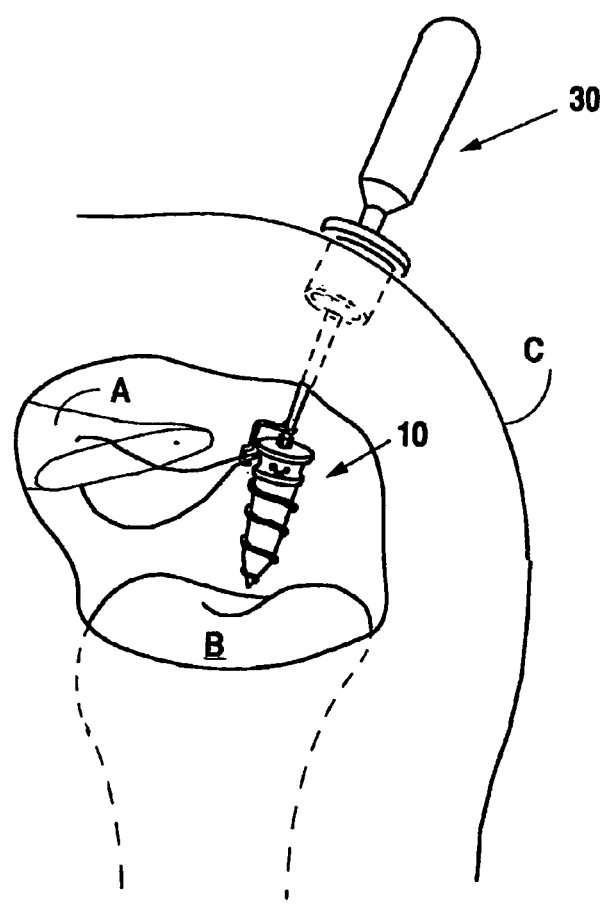

FIGS. 1 and 2 also illustrate how the tool 30, such as the tool illustrated in FIG. 4, is used to engage walls 12C of the head 12 in a manner such that, when the tool 30 (see FIG. 4) is engaged with the suture anchor 10 and, further, while the suture member 40 is engaged with the walls of the shank portion 14, the suture member 40 will gather on the reel portion 22 of the suture anchor 10. Further, since the suture member 40 was previously engaged with, as by threading a tissue A (see FIG. 3A illustrating open surgery rather than arthroscopic, a suture passer would be used in arthroscopic surgery) before being engaged with the suture member 40, rotation and gathering of the suture member 40 on the reel portion 22 of the suture anchor 10 will cause the tissue to move closer to the suture anchor 10 while the suture anchor 10 is being driven into bone, so as to simultaneously affix the suture anchor 10 to the bone and gather the suture member 40 onto the suture anchor 10 to position the tissue adjacent the bone at a predetermined location.

FIG. 6 illustrates the use of Applicant's novel method, device, and kit when the task of reeling up suture material is completed so as position tissue A against or adjacent bone mass B at a predetermined position flush with bone or countersunk to produce an interference fit with the suture material between the anchor and the bone. Alternatively, a portion of the reel portion may be left above the surface of the bone.

It is anticipated that Applicant's novel method, device and kit is best utilized with arthroscopic techniques through the use of cannula D, here illustrated for use on a shoulder, but capable of being used anywhere in the body where tissue is needed to be attached to a bone mass. Indeed, Applicant's method and system can be used in open surgery as well as arthroscopically. When used in arthroscopic surgery, the suture anchor 10 is usually dimensioned suitable to fit within the cannula D, as is the tool 30.

As shown in FIG. 5, a hook device 60 may be inserted through the cannula D and used when either additional suture material 40 needs to be taken up and wound around the reel manually, as when the suture anchor 10 is already seated into the bone, and the tissue needs to be brought yet closer to the anchor. Likewise, suture material may be unwound one course at a time if the surgeon feels it is necessary to allow the tissue to move further from the inserted suture anchor 10.

The following describes the novel method (open or arthroscopic) of use of Applicant's present invention. The repair site is first located after a small incision and insertion of the cannula D through the skin. The suture member 40 is threaded onto a needle (open surgery) or suture passer (arthroscopic surgery), which is transported to the repair site. The suture-bearing needle or arthroscopic instrument is passed through the tissue, and then the suture member 40 and the needle are removed through the cannula D. The suture member 40 is then engaged with the suture anchor 10 by, for example, inserting through the holes 24 in the suture anchor 10 and tied off or pulled through the hole (FIG. 3). Alternatively, the suture may pass through the hole and not be tied, but simply wound around the reel portion for a friction fit to the anchor. Next, the suture anchor 10 is transported through the cannula D to the repair site and placed adjacent the bone mass positioned selectively so that rotation and insertion of the suture anchor 10 into the bone mass, while the suture member 40 is winding onto the reel portion, will locate the tissue at a predetermined location adjacent the bone mass. If the anchor is made from a bioabsorbable material, the bone is typically pre-tapped before inserting the anchor.

Having selected the appropriate location adjacent the bone mass, the tool 30 is then inserted through the cannula D and engaged with the head of the suture anchor 10. Rotation by manually rotating the handle of the tool 30, while urging the suture anchor 10 against the bone, will seat the suture anchor 10 while the suture member 40 winds onto the reel portion 22 of the suture anchor 10. Rotation continues until the tissue is properly positioned adjacent the bone mass with anchor sunk until head upper surface is flush with cortex of bone or countersunk (see FIG. 6). This provides an interference fit holding the suture between the bone and the reel portion so the suture material will not unwind. Alternate procedures, such as using the hook tool 60 through the wind or unwind courses of the suture member 40 onto the reel portion 12, used if necessary. The tool 60 and the cannula D are then removed and the wound closed in accordance with procedures known in the art.

The surgeon may estimate the amount of take up required on the suture material to properly locate the tissue. Knowing the approximate diameter of the reel portion, the surgeon may adjust the pre-drilling length of suture between the anchor and the tissue so that when the anchor is wound into the bone to the position set forth in FIG. 6, the tissue is properly positioned.

FIG. 7 illustrates an embodiment wherein reel portion 12 is anywhere along the shank portion. The interference fit of the suture between the anchor and the bone will be greater as the reel is positioned closed to the tip.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

The invention claimed is:

1. A method of anchoring tissue to bone using suture comprising, in the recited order, the steps of:
   providing an anchor comprising a head portion with walls adapted to receive an anchor driver; and, a shank portion with outer walls, the shank with a channel therein, the channel connecting openings in the outer walls of the shank;
   engaging the suture to the tissue;
   threading suture so it is entrained in the channel of the anchor; and
   inserting the anchor into the bone such that the suture lies wedged between and substantially contacting and directly engaging the bone and the walls of the anchor in an interference fit.

2. The method of claim 1, wherein the anchor has a ridge member to assist in obtaining the interference fit of the inserting step.

3. The method of claim 2, wherein the ridge has a greater diameter than the walls adjacent the channel receiving the suture.

4. The method of claim 3, wherein the inserting is sufficient to position the head below the bone surface.

5. The method of claim 3, wherein the inserting step inserts the anchor such that the head is at least flush with the surface of the bone.

6. The method of claim 5, further including the step of adjusting the suture so the tissue lies at a preselected location, such adjusting of the suture prior to inserting the anchor.

7. A method of anchoring tissue adjacent bone, the method comprising, in the recited order, the steps of:
  providing an anchor with outer walls having a ridge thereon;
  threading a tissue with a suture;
  engaging the suture to the anchor;
  selecting a site on a bone for anchor insertion;
  positioning the tissue with the suture attached adjacent the selected site; and
  driving the anchor into the hole so the suture is wedged between the walls of the hole and the anchor in an interference fit directly engaging the bone and anchor;
  wherein said driving step includes rotation of the anchor such that the suture winds around the anchor.

8. The method of claim 7, wherein the driving step includes driving the anchor such that the ridge is at least flush with the surface of the bone.

9. The method of claim 7, wherein the driving step drives the anchor into the bone such that the ridge is below the surface of the bone.

10. The method of claim 7, further including providing a tool with a suture engagement means; and, further including the step of engaging the tool with the anchor and the suture so as to position the suture adjacent the anchor during the driving step.

11. The method of claim 7, wherein the driving step includes driving the anchor such that the ridge is at least the depth of the surface of the bone, further including providing a tool with a suture engagement means, further including the step of engaging the tool to the anchor and to the suture so as to position the suture adjacent the anchor during the driving step.

12. The method of claim 7, further including the step of providing a tool with a suture engagement means, further including the step of engaging the tool to the anchor and to the suture so as to position the suture adjacent the anchor during the driving step, wherein the driving step drives the anchor into the bone such that the ridge is below the surface of the bone.

13. A method for using a suture anchor having a suture receiving portion, the method comprising, in the recited order, the steps of:
  (a) passing a suture member through tissue;
  (b) engaging the suture member with the suture anchor; and
  (c) driving the suture anchor longitudinally into the bone such that the suture member assumes an interference fit directly engaging both the suture and the bone; wherein said inserting step includes rotation of the anchor such that the suture winds around the anchor.

14. The method of claim 7, wherein said inserting step includes rotation of the anchor such that the suture winds around the shank.

15. The method of claim 1, further including the step of providing the anchor driver for engagement with the anchor and further including the step of engaging the anchor driver to the anchor so as to avoid engagement of the anchor driver with the suture.

16. The method of claim 7, further including the step of providing an anchor driver for engagement with the anchor and further including the step of engaging the anchor driver to the anchor so as to avoid engagement of the anchor driver with the suture.

17. The method of claim 1, wherein said inserting step includes rotation of the anchor such that the suture winds around the shank; and further including the step of providing the anchor driver for engagement with the anchor and further including the step of engaging the anchor driver to the anchor so as to avoid engagement of the anchor driver with the suture.

18. The method of claim 7, wherein said inserting step includes rotation of the anchor
  such that the suture winds around the shank; and further including the step of providing an anchor driver for engagement with the anchor and further including the step of engaging the anchor driver to the anchor so as to avoid engagement of the anchor driver with the suture.

19. A method of anchoring tissue to bone using suture comprising, in the recited order, the steps of:
  providing an anchor comprising a head portion with walls adapted to receive an anchor driver; and, a shank portion with outer walls, the shank with a channel therein, the channel connecting openings in the outer walls of the shank;
  engaging the suture to the tissue;
  threading suture so it is entrained in the channel of the anchor; and
  inserting the anchor into the bone such that the suture lies wedged between the bone and the walls of the anchor in an interference fit so the suture directly engages both the bone and walls of the anchor;
  wherein the inserting step moves the anchor longitudinally into the bone while simultaneously positioning the tissue adjacent the bone, the inserting step continuing until the anchor is at or below the bone surface.

* * * * *

UNITED STATES PATENT AND TRADEMARK OFFICE
CERTIFICATE OF CORRECTION

| | | |
|---|---|---|
| PATENT NO. | : 7,959,649 B2 | |
| APPLICATION NO. | : 11/637383 | |
| DATED | : June 14, 2011 | |
| INVENTOR(S) | : Stephen S. Burkhar | |

It is certified that error appears in the above-identified patent and that said Letters Patent is hereby corrected as shown below:

In the Specification

At col. 1, line 7, "and claims priority from" should read -- which is a continuation of U.S. Patent Application No. 09/825,110, filed April 3, 2001 and issued as --.

At col. 1, line 8, "and" should read -- which is a continuation of U.S. Patent Application No. 09/322,371, filed on May 28, 1999 and issued as --.

Signed and Sealed this
Sixth Day of May, 2014

Michelle K. Lee
*Deputy Director of the United States Patent and Trademark Office*